(12) United States Patent
Brady et al.

(10) Patent No.: US 6,447,519 B1
(45) Date of Patent: *Sep. 10, 2002

(54) APPARATUS FOR HOLDING INTRAOCULAR LENSES AND INJECTORS, AND METHODS FOR USING SAME

(75) Inventors: Daniel G. Brady, San Juan Capistrano; Arlene Gwon, Newport Beach; Michael Collinson, Goleta; Claude A. Vidal, Santa Barbara; Alan K. Plyley, Goleta, all of CA (US)

(73) Assignee: Allergan Sales, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/532,460

(22) Filed: Mar. 22, 2000

Related U.S. Application Data (62) Division of application No. 09/292,146, filed on Apr. 15, 1999, now Pat. No. 6,129,733.

(51) Int. Cl.⁷ .................................................. A61F 9/00
(52) U.S. Cl. ....................................................... 606/107
(58) Field of Search .......................................... 606/107

(56) References Cited

U.S. PATENT DOCUMENTS

| 4,836,201 A | 6/1989 | Patton et al. |
| 5,171,241 A | 12/1992 | Buboltz et al. |
| 5,176,686 A | 1/1993 | Poley |
| 5,578,042 A | 11/1996 | Cumming |
| 5,582,614 A | 12/1996 | Feingold |
| 5,643,276 A | 7/1997 | Zaleski |
| 5,891,152 A | 4/1999 | Feingold |
| 5,947,974 A | 9/1999 | Brady et al. |
| 6,129,733 A | * 10/2000 | Brady et al. ................ 606/107 |

FOREIGN PATENT DOCUMENTS

| WO | 9820819 | 5/1998 |
| WO | 9929267 | 6/1999 |

* cited by examiner

Primary Examiner—Paul J. Hirsch
(74) Attorney, Agent, or Firm—Stout, Uxa, Buyan & Mullins, LLP; Franc J. Uxa (57) ABSTRACT

Apparatus for holding intraocular lenses and apparatus for holding intraocular lens injectors are provided which provide convenient and effective packaging systems for intraocular lenses and allow convenient and effective transfer of an intraocular lens to an injector in preparation for insertion of the intraocular lens into an eye.

14 Claims, 4 Drawing Sheets

APPARATUS FOR HOLDING INTRAOCULAR LENSES AND INJECTORS, AND METHODS FOR USING SAME

This is a divisional of application Ser No. 09/292,146, filed Apr. 15, 1999 now U.S. Pat. No. 6,129,733.

FIELD OF THE INVENTION

This invention relates generally to intraocular lenses and injectors and, more particularly, to apparatus for holding intraocular lenses, apparatus for holding intraocular lens injectors, combinations including such apparatus and methods for loading intraocular lens into injectors using such apparatus and combinations.

BACKGROUND OF THE INVENTION

As is well known, intraocular lenses or IOLs are used in the eye, for example, as an adjunct to the natural lens of the eye or to replace the natural lens of the eye when the natural lens becomes damaged or otherwise incapable of functioning. For example, the natural lens may be removed and an IOL is inserted into the eye as a direct replacement. A typical IOL includes an optic or lens body for focusing light toward the retina of the eye, and one or more fixation members or haptics for fixing the IOL in the desired position within the eye.

The IOL preferably is implanted directly into the eye through a small incision formed in the ocular tissue of the eye. To fit through this small incision, optics of modern IOLs are designed to be deformed, e.g., folded, rolled or the like, to a relatively small profile and then allowed to substantially return to their original shape within the eye.

The IOL is typically provided to the surgeon or other medical personnel in a packaging system which contains the IOL. These packaging devices protect the IOL during handling and transportation to the surgical site and may even allow for accurately folding the IOL along the optic diameter in order to reduce its size. Some of these systems specifically fold the IOL in preparation for grasping by the forceps or other surgical instrument. One form of such a holding and folding device or system is described in Buboltz et al U.S. Pat. No. 5,171,241.

A very useful technique for inserting an IOL into the eye includes the use of an IOL injector or cartridge, such as the IOL injector described in Bartell, U.S. Pat. No. 4,681,102. These IOL injectors include a load chamber which is connected to an injection tube. The load chamber includes an openable first lumen for receiving the IOL. Closure of this first lumen folds the IOL and maintains the IOL in a folded state. The injection tube includes a small diameter distal tip which is insertable into the incision within the eye. The IOL is transferable from the load chamber through the injection tube and into the eye. These IOL injectors simplify the placement of the IOL within the eye and reduce chances of surgeon error.

A very useful IOL packaging system is disclosed in commonly assigned U.S. patent application Ser. No. 08/987,864, filed on Dec. 9, 1997, the disclosure of which is hereby incorporated in its entirety herein by reference. The IOL is placed on the load chamber so that the IOL will be folded when the load chamber is closed.

The technique of transferring the IOL to the load chamber of the injector normally is accomplished by manually manipulating the IOL and/or injector. Such manual manipulation requires a relatively high degree of dexterity and can result in the IOL being incorrectly loaded in the injector. Also, increased handling increases the risk of damaging and/or contaminating the IOL and/or injector.

It would be advantageous to provide an IOL injector holding system so that the IOL could be placed in the injector with reduced, or even substantially no, manual manipulation.

SUMMARY OF THE INVENTION

Apparatus for holding intraocular lens injectors, combinations of intraocular lens injector holding assemblies and intraocular lens holding assemblies, intraocular lens packaging systems and methods for using intraocular lens injector holding apparatus and assemblies have been discovered. The present intraocular lens injector holding apparatus and assemblies provide enhanced ease of use, for example, by requiring reduced dexterity to load an IOL into an injector and/or by simplifying or eliminating individual steps previously required to load the IOL. For example, the IOL injector preferably does not have to be manually handled except to place the injector into an injector system hand piece for insertion of the IOL into the eye. The present invention reduces the risk of dust or other contamination on the IOL, as well as reducing the risk of damaging the IOL injector. Additional benefits include the provision for holding a soft tip for use on a push rod of the IOL injection system. Also, additional lubricants, such as aqueous balanced salt solution (BSS) and/or visco elastic materials, can be added in the injector while it is still being held by the holding apparatus or assembly. The present apparatus, combinations, systems and methods are straightforward in construction and are relatively easy and convenient to manufacture, use and practice.

In one broad aspect of the present invention, apparatus for holding an intraocular lens injector or cartridge having a load or loading chamber, and preferably a pair of generally opposing wings, so that the loading chamber is maintained in an open position are provided. The apparatus comprises a housing and at least one element, preferably a plurality of such elements. The housing is sized and adapted to receive the intraocular lens injector. The element or elements are secured to the housing and are adapted and positioned to stabilize the position of the intraocular lens injector relative to the housing, for example, to hold the intraocular lens injector in or to the housing, with the loading chamber in the open position.

The present apparatus for holding an intraocular lens injector may be considered a package system for such intraocular lens injectors. Thus, the intraocular lens injector may be included with the apparatus at the point of manufacture or assembly of the intraocular lens injector. In this fashion, the surgeon or technician at the surgical site does not need to handle the intraocular lens injector prior to placing the intraocular lens into the injector.

Preferably, the intraocular lens injector has a proximal end, and one of the elements of the present apparatus is positioned to be in proximity, or even substantially abutting relation, to this proximal end. The intraocular lens injector includes an injection tube located distally of the loading chamber. One or more of the elements of the present apparatus preferably are positioned to contact the injection tube, for example, to stabilize the position of the injection tube, and more preferably to hold the injector to the housing. In a useful embodiment, one or more elements are positioned to be in proximity to the proximal end of the injector and one or more elements are positioned to contact the injection tube. Other configurations of these elements may be employed and are included within the scope of the present invention. These elements preferably are positioned so as to facilitate maintaining the injector in a substantially fixed position so that the intraocular lens can be placed in the loading chamber in the proper orientation for insertion into the eye.

The present intraocular lens injector holding apparatus preferably further include support members secured to the housing and adapted and positioned so that at least one of the support members is in close proximity to each of the wings of the received intraocular lens injector. Thus, both wings are provided with such support member or members located in close proximity thereto, for example, so that the wings are effectively positioned to facilitate the use of the injector holding apparatus with the intraocular lens holding assembly, as is discussed elsewhere herein.

The housing may include a base, with the element or elements secured to the base and extending therefrom.

In one embodiment, the housing includes a sidewall extending from, preferably extending generally upwardly from, the base. More preferably, the housing includes a peripheral sidewall which substantially fully or completely circumscribes the base. Such sidewall is effective, for example, to protect the intraocular lens injector during shipment, storage and handling.

In a very useful embodiment, the sidewall includes at least one projection extending inwardly. The injector holding apparatus further comprises at least one mounting member secured to the housing and spaced apart from the at least one projection. Preferably, the apparatus includes two of these projections and two of the mounting members positioned so that each projection is aligned with and spaced apart from a different mounting member. The projection or projections and mounting member or members combinations are very effective in facilitating the placement of the intraocular lens into the intraocular lens injectors, as is described elsewhere herein.

The present intraocular lens injector holding apparatus advantageously further comprises a tip holder secured to the housing, preferably to the base of the housing. This tip holder is sized and adapted to hold a tip, for example, a soft tip made of polymeric material, such as silicone polymeric material, to be placed on the distal end of a push rod used in inserting an intraocular lens into the eye. Thus, the present intraocular lens injector holding apparatus not only provides for an easy and convenient way to provide the IOL in the injector, but also preferably allows the surgeon to very conveniently place the tip on the push rod prior to inserting the IOL into the eye.

The present intraocular lens injector holding apparatus preferably are made of polymeric materials, although other materials of construction may be employed. In one very useful embodiment, the present apparatus are unitary in construction, that is have a single piece construction.

In another broad aspect of the present invention, useful combinations are provided which comprise an intraocular lens injector holding assembly and an intraocular lens holding assembly. An intraocular lens injector or cartridge may be removably held to the injector holding assembly. An IOL, including a deformable optic, may be removably retained by the intraocular lens holding assembly. The injector holding assembly and the intraocular lens holding assembly are adapted to cooperate in transferring the intraocular lens to the injector. The intraocular lens holding assembly preferably is further adapted to receive and hold the intraocular lens injector. The injector holding assembly and lens holding assembly advantageously are further adapted to cooperate to directly transfer the injector from the injector holding assembly to the lens holding assembly. In one embodiment, the lens holding assembly is still further adapted so that the transferred injector is manually removable from the lens holding assembly together with the IOL. The injector, with the IOL positioned therein, can then be used in inserting the IOL into an eye.

The intraocular lens injector holding assemblies of the present combinations preferably are similar in structure and functioning to the injector holding apparatus described herein and comprise a housing and at least one element, preferably a plurality of elements. The housing is sized and adapted to receive an intraocular lens injector having a loading chamber, and preferably a pair of generally opposing wings, so that the loading chamber is maintained in an open position. The element or plurality of elements are secured to the housing and are adapted and positioned to stabilize the position of the injector relative to the housing, preferably to hold the intraocular lens injector in or to the housing, with the loading chamber in the open position.

The intraocular lens holding assemblies of the present combinations are adapted for removably retaining an IOL, and preferably comprise a holding member having a first side and a substantially opposing second side, and more preferably a hinge, such as a centrally located, longitudinally extending hinge. In one embodiment, the holding member includes a plurality of retaining members extending from the first side and adapted to receive and removably retain the intraocular lens injector. The intraocular lens holding assembly may be considered at least a portion of a packaging system for the IOL.

In one very useful embodiment, the second side of the holding member includes at least one indent, more preferably a hole through the holding member, and the housing includes at least one projection adapted to be introduced into the at least one indent to facilitate the direct transfer of the intraocular lens from the holding member to the intraocular lens injector. More preferably, two spaced apart indents are provided in the holding member and two corresponding or complementary spaced apart projections are included in the housing.

At least one of the housing and the holding member, more preferably both the housing and the holding member, are structured to facilitate the proper positioning of the intraocular lens injector holding assembly and the intraocular lens holding assembly to facilitate the transfer of the injector to the holding member and/or the IOL from the holding member to the intraocular lens injector. For example, the sidewall of the housing may include an off-center, inwardly extending indexing projection (or recess) and the holding member may include a complimentarily sized, off-center indexing recess (or projection). The indexing projection and recess are oriented so that the projection and recess are in mating relation when the housing and holding member are properly positioned to facilitate the direct transfer of the injector to the holding member. This feature very effectively reduces, or even substantially eliminates, the risk of the IOL ultimately becoming improperly placed in the injector.

In a very useful embodiment, the holding member defines a slot, for example, a slot defined by a groove, sized and adapted for removably retaining the intraocular lens.

In an additional aspect of the invention, package systems for intraocular lenses are provided and comprise an elongated holding member and a cover member. The holding member includes a first portion and a second portion with the first portion being adapted for removably retaining an intraocular lens. The cover member includes a top and a bottom and is adapted to receive the first portion of the holding member. The cover member is further adapted to be movable between a closed position surrounding the first portion and an open position to allow the holding member to be removed from the cover member. The second portion of the holding member preferably extends outside the cover member while the first portion is received by the cover member and the cover member is in the closed position. The top and the bottom of the cover member preferably are formed as a unitary structure which further includes a hinge located between the top and the bottom, for example, to facilitate the movement of the cover member between the closed and open positions.

In a particularly useful embodiment, the top of the cover member includes a first fastener member and the bottom of the cover member includes a second fastener member positioned and adapted to cooperate with the first fastener member to hold the cover member in the closed position. The first and second fastener members preferably can be operated by one hand of an adult human to open and close the cover member, as desired. The holding member and the cover member advantageously are configured to removably hold the holding member to the cover member when the holding member is received by the cover member.

The present IOL package systems very effectively protect the intraocular lens during transportation and storage. Since the elongated holding members of the present IOL package systems may, and preferably are, substantially similar to the holding members described elsewhere herein, such elongated holding members can be effectively used in transferring the IOL to an IOL injector, as described herein.

In a still further broad aspect of the present invention, methods for loading IOLs into an injector in preparation for inserting the IOL into an eye are provided. The injector has a load or loading chamber. The present methods comprise:

providing a deformable IOL in an intraocular lens holding assembly adapted for removably retaining the IOL;
 providing the injector held in an intraocular lens injector holding assembly including a housing side and adapted to receive the injector so that the loading chamber is maintained in an open position;
 positioning the holding member in close proximity to the housing; and
 moving the holding member relative to the housing to effect the direct transfer of the injector from the intraocular lens injector holding assembly to the intraocular lens holding assembly.

The present methods preferably further provide for removing the injector and the intraocular lens together from the intraocular lens holding assembly. The injector and IOL can then be placed in an IOL injector system handpiece, of conventional construction. The IOL in the injector, with the injector in the handpiece, is available for insertion into an eye.

The present intraocular lens injector holding assemblies and/or intraocular lens holding assemblies can very effectively be used in the present methods.

Any and all features described herein and combinations of such features are included within the scope of the present invention provided that the features of any such combination are not mutually inconsistent.

Additional aspects and advantages of the present invention are set forth in the following description and claims, particularly when considered in conjunction with the accompanying drawings in which like parts bear like reference numerals.

DETAILED DESCRIPTION OF THE DRAWINGS

Figure 1:
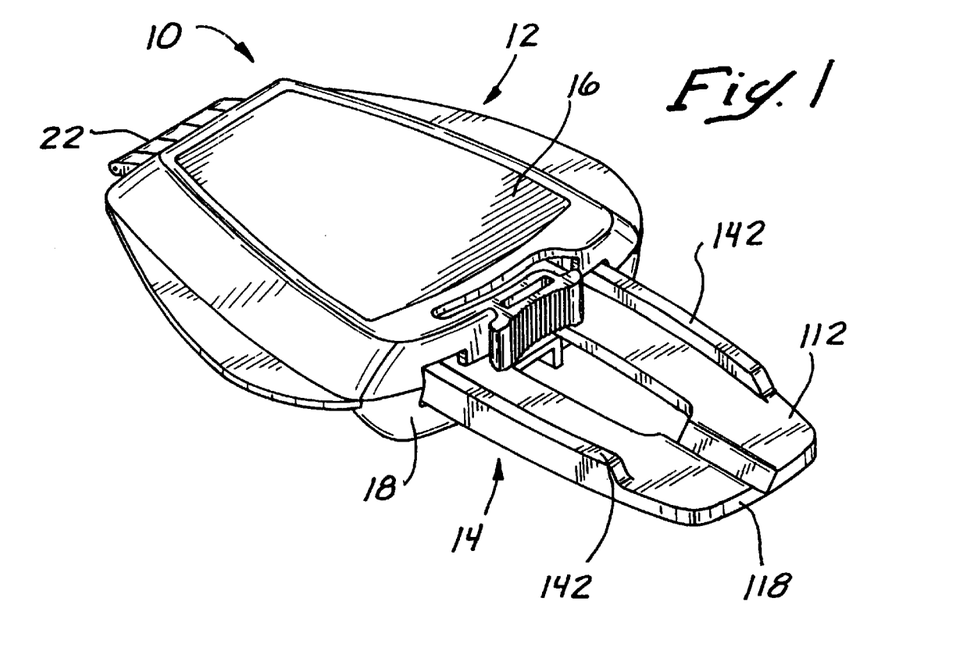
FIG. 1 is a perspective view of an intraocular lens package system in accordance with the present invention.
Figure 2:
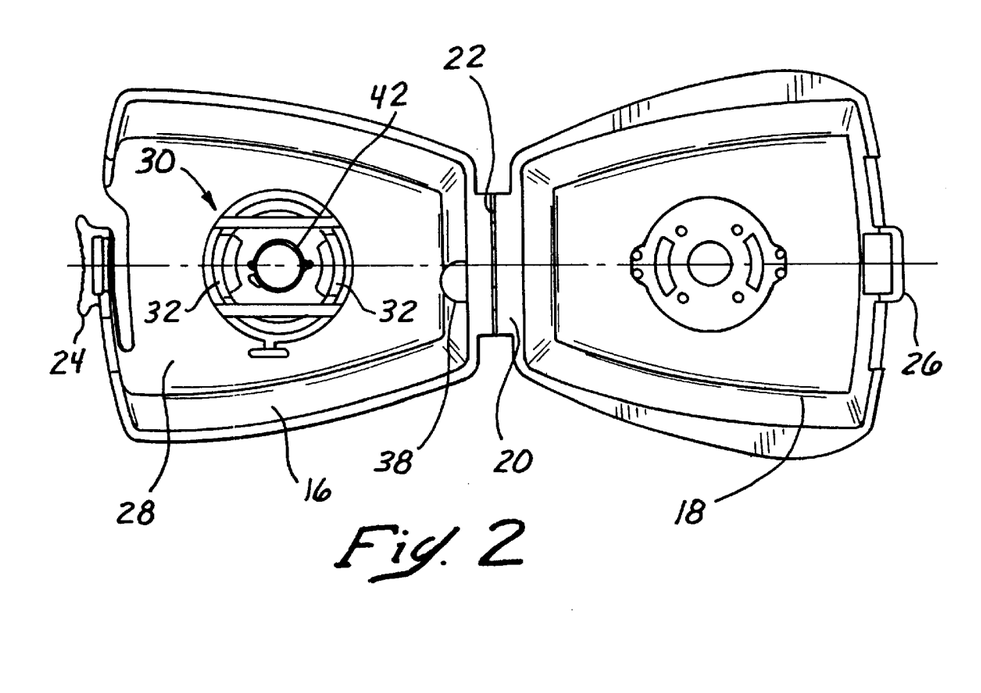
FIG. 2 is a plan view of the inside of the cover of the package system shown in FIG. 1

Referring now to FIGS. 1 and 2, an IOL package system in accordance with the present invention is shown generally at 10. Package system 10 includes a cover 12 and an elongated IOL holding member 14. Cover 12 is molded out of a thermoplastic polymeric material, such as polypropylene, and includes a top cover 16, a bottom cover 18, and an intermediate area 20 joining the top and bottom covers. A hinge 22, of conventional construction, is positioned in the intermediate area 20 and facilitates moving the cover 10 between the closed position (FIG. 1) and the open position (FIG. 2). Cover 12 can be a unitary structures with one or more hinges, preferably a single hinge, e.g., a living hinge, between the top and bottom covers.

Top cover 16 includes a first fastener component 24, while bottom cover 18 includes a second fastener component 26. When cover 12 is located in the closed position, the first fastener component 24 captures and holds the second fastener component 26. When it is desired to open cover 12, the first fastener component 24 can simply be pressed in, which releases the second fastener component 26 and allows the cover to be opened. The fastener including fastener components 24 and 26 is of conventional design. Other fasteners may be employed and are included within the scope of this invention. One advantage of the fastener combination 24 and 26 is that it can be operated using a single hand of a human user who is also holding the system 10.

Figure 3:
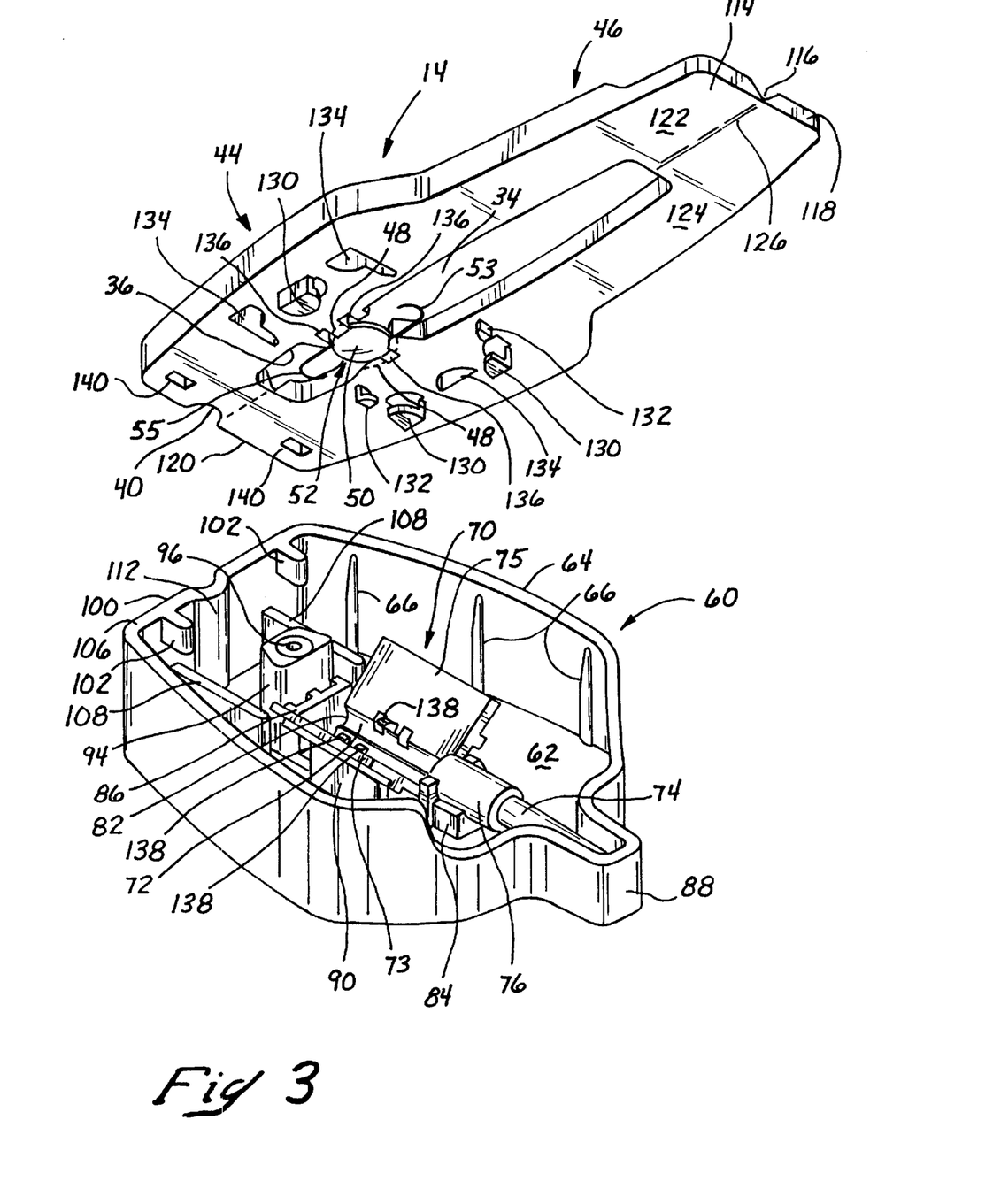
FIG. 3 is a perspective view of an embodiment of a combination of an intraocular lens holding assembly and an intraocular lens injector holding assembly in accordance with the present invention.

The inner surface 28 of top cover 16 includes a central area 30 including a plurality of features which facilitate placing the IOL holding member 14 in association with cover 12. Specifically, central area 30 includes two upwardly extending pegs 32 which fit into first opening 34 and second opening 36 of IOL holding member 14 (FIG. 3). With the pegs 32 in place in the openings 34 and 36 and the cover 12 in the closed position, the IOL holding member 14 is held substantially stationary by the cover. In addition, the intermediate region 20 includes a projection 38 which extends inwardly toward the central area 30. This projection 38 is off-center and is shaped to compliment the off-center recess 40 of holding member 14 (FIG. 3). Thus, when placing the holding member 14 in the open cover 12, the projection 38 mates with the recess 40 to insure that the holding member is properly placed within the cover.

Central area 30 also includes a central plateau 42 which is positioned to provide support for the IOL 52 (FIG. 3) being held by the holding member 14.

The IOL holding member 14 is described with reference to FIGS. 1 and 3. Holding member 14 includes a first portion 44 and a second portion 46. Second portion 46 extends outside the cover 12 when the cover is in the closed position (FIG. 1). First portion 44, which defines an internal groove 38 for removably retaining the optic 50 of IOL 52, is located within the cover 12 with the cover in the closed position. IOL 52 includes deformable optic 50, for example, made of silicone polymeric material, flexible or foldable acrylic polymeric material and the like. Filament fixation members or haptics 53 and 55 of IOL 52 are coupled to the optic 50 and can be made of any suitable material such as a polymeric material, for example, polypropylene, polymethyl methacrylate (PMMA) and the like. The haptics 53 and 55 are positioned generally parallel to the length of holding member 14. Holding member 14 preferably is a unitary structure, for example, molded of thermoplastic polymeric materials, such as polypropylene and the like.

Package system 10 is used as follows. When it is desired to ship IOL 52, the optic 50 of the IOL is placed in the internal groove 48 of holding member 14 (as shown in FIG. 3). The holding member 14 is then positioned relative to the top member 16 of cover 12 with the pegs 32 located in the first opening 34 and second opening 36 of the holding member and the projection 38 of the cover mated to the recess 40 of the holding member. The cover 12 is then placed in the closed position and the package system 10, including IOL 52, is ready for shipment. The IOL 52 in the package system 10 can be conveniently and safely shipped, for example, from the IOL manufacturing site to the surgical site. IOL 52 preferably is subjected to a conventional sterilization procedure prior to being included in package system 10. The package system 10 itself preferably is subjected to a conventional sterilization procedure and, with the IOL 52 in place in the package system, may be included in a suitable bag or other container to maintain satisfactory sterility during shipment.

Once the package system 10 is at the surgical site and the IOL 52 is selected for insertion into an eye, the cover 12 is placed in the open position and the holding member 14 is removed from the cover. The IOL 52 may then be removed for the holding member 14, as is described hereinafter, and inserted into an eye. The package system 10 preferably is disposed of after a single use.

Figure 4:
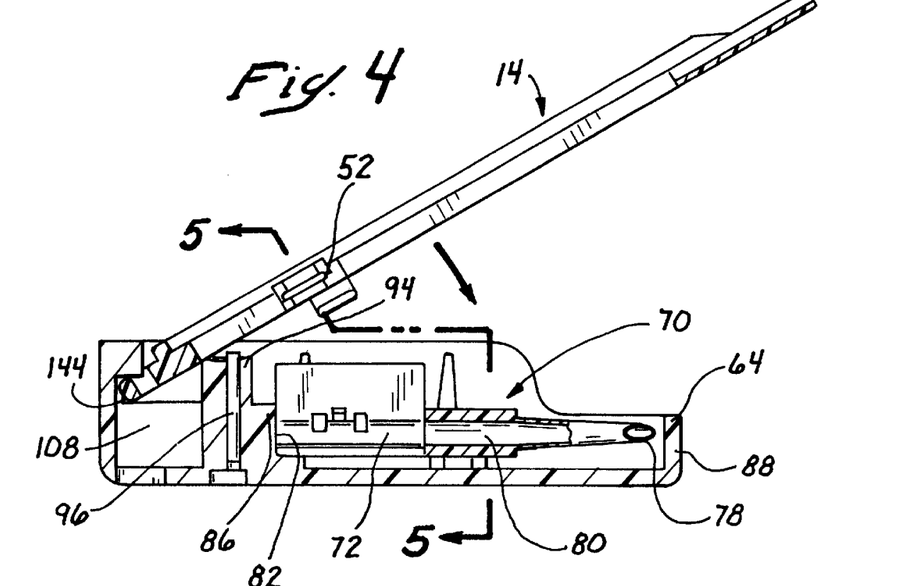
FIG. 4 is a side view, in cross section, of the combination shown in FIG. 3 with the intraocular lens holding assembly positioned in initial contact with the intraocular lens injector holding assembly.

With reference to FIG. 3, the holding member 14 can be used in combination with an injector holder, shown generally at 60. Injector holder 60 includes a base 62 and a peripheral sidewall 64 which fully circumscribes the base. The combination of base 62 and sidewall 64 can be considered a housing. Reinforcing ribs 66 are provided around sidewall 64 to maintain the structural integrity of the injector holder 60. An IOL injector, shown generally at 70, includes a loading chamber 72, and an injection tube 74 which is partially defined by an enlarged reinforcing collar 76. With reference to FIG. 4, the injection tube includes a right-facing distal end opening 78 through which an IOL which is included in injector 70 passes for insertion into an eye. The combination of the loading or load chamber 72 and the injection tube 74 defines a hollow space or passage 80 through which the IOL passes in being inserted into the eye. Injector 70 also includes a proximal end 82.

As shown in FIG. 3, injector 70, and in particular loading chamber 72, is shown in an open position. A front element 84, secured to base 62, extends upwardly and comes in contact with the reinforcing collar 76 of injection tube 74. The front member 84 is configured to cradle or hug the reinforcing collar 76 in a substantially snug or even grasping fit. This substantially snug or grasping fit is sufficient to hold injector 70 to injector holder 60. Back element 86, which also is secured to and extends upwardly from base 62, is positioned to be in relatively close proximity to the proximal end 82 of injector 70. Back element 86 is effective to stabilize the position of the injector 70 in injector holder 60, particularly in combination with front element 84 and the front end 88 of sidewall. 64.

Support members 90 (FIGS. 3 and 5) are secured to and extend upwardly from base 62 and are effective to maintain the wings 73 and 75 of injector 70 in an open position and available to cooperate with the IOL holding member 14, as is described hereinafter.

A tip holder 94 is secured to and extends upwardly from base 62 and is configured to hold a soft tip 96, made of soft polymeric material, which is structured to fit onto the distal end of a push rod used in inserting an IOL into the eye through the injector 70. The back portion 100 of sidewall 64 includes two spaced apart projections 102. These spaced apart projections 102 extend inwardly toward the injector 70 and are located near the top end 106 of the sidewall 64. A pair of mounting members 108 are secured to and extend upwardly from the base 62 and are generally aligned and spaced apart from projections 102, as shown best in FIG. 3.

In addition, the back portion 100 of sidewall 64 includes an inwardly extending, off-center indexing projection 112 which cooperates with the recess 40 of holding member 14, as is described hereinafter.

Injector holder 60 preferably is a unitary structure and may be produced, e.g., molded, from any suitable material of construction, such as thermoplastic polymeric materials, for example, polyethylene and the like.

With reference to FIGS. 1 and 3, holding member 14 includes a first side 112 and a second side 114. A longitudinally extending living hinge 116 extends from the front end 118 to the back end 120 of holding member 14 and is centrally located, that is hinge 116 divides holding member 14 into two generally equally sized halves 122 and 124 along fold axis 126.

Figure 7:
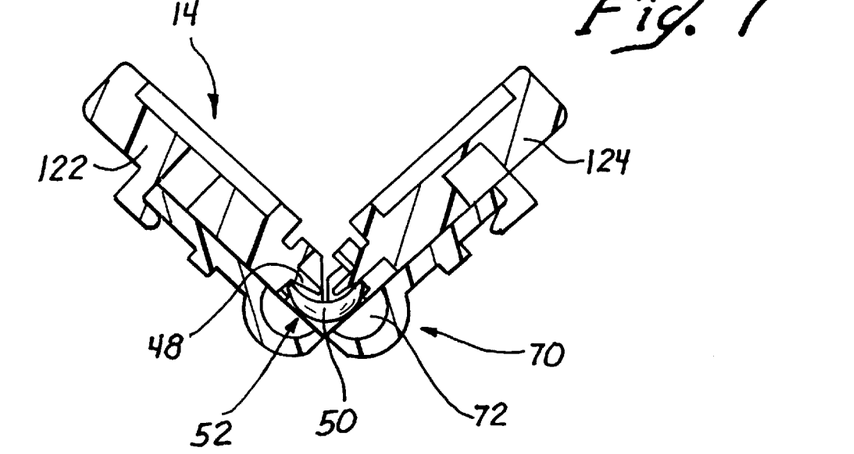
FIG. 7 is a cross sectional view of the intraocular lens holding assembly holding the IOL injector and being located in a bent condition.

Hinge 116 pivotally couples first and second halves 122 and 124 of holding member 14 about fold axis 126. Preferably, the hinge 116 includes a pair of spaced apart hinge portions aligned along the fold axis 126 with first and second openings 34 and 36 therebetween. The hinge 116 allows the first and second halves 122 and 124 to fold towards each other from a planar position, for example, as illustrated in FIG. 7.

Each of the first and second halves 122 and 124 includes a portion of internal groove 48 specifically configured for retaining the IOL 52. Preferably, each of these portions of groove 48 comprises an opposing internal cutout for receiving a portion of the optic 50. Each portion may be sized and dimensioned to receive and retain an edge of the optic 50.

A plurality of retaining brackets 130 are secured to and extend outwardly from the second side 114 of holding member 14. The first half 122 of holding member 14 includes a single retaining bracket 130 and the second half 124 includes a pair of spaced apart retaining brackets 130, somewhat differently configured from and generally opposing the retaining bracket 130 on the first half. The retaining brackets 130 are sized and configured for receiving and removably retaining or holding the IOL injector 70 to the lens holder 14, as is described hereinafter.

Two spaced apart constraints 132 are secured to and extend from second side 114 and are sized and positioned to guide the IOL injector 70 into the retaining brackets 130.

An opening 134 is located in second half 124 and does not extend through the holding member 14. This opening 134 is configured for receiving the retaining bracket 130 on the first half 122. The first half 122 includes a pair of spaced apart openings 134 which do not extend through the holding member 14 and are configured for receiving the retaining brackets 130 and constraints 132 on second half 124.

The openings 134 allow the halves 122 and 124 to fold together about a first direction such that the two halves lie flat against each other in a folded position. Thus, although it is not preferred, the present holding member 14, and IOL package system 10, can be employed when the IOL 52 is to be removed from the holding member 14 using a forceps. Thus, when a forceps is to be so used, the two halves 122 and 124 of the holding member 14 are folded along fold axis 126 to lie substantially flat against each other. This action exposes the IOL 52 retained by the holding member 14 so that it can be removed from the holding member in a folded condition using a forceps. The folded IOL 52 can then be inserted directly into an eye or placed in an IOL delivery system suitable for inserting the IOL in an eye.

The second side 114 includes a plurality of grooves 36. Such grooves 136 are positioned generally transverse to the internal groove 48 and extend to the internal groove 48. The grooves 136 are configured and oriented for use with injector 70 which includes grasping fingers 138.

The holding member 14 includes two spaced apart through holes or recesses 140 located near the back end 120.

In addition, each of the first and second halves 122 and 124 include longitudinally extending handling ribs 142 which extend upwardly from the first side 112 and extend from the first portion 44 to the second portion 46 and terminate short of front end 118 of holding member 14. Ribs 142 are effective in allowing the user to conveniently handle and manipulate the holding member 14.

Figure 5:
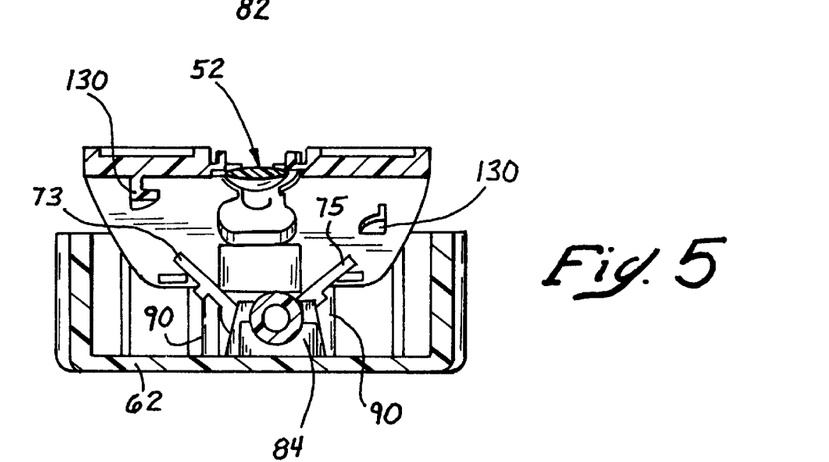
FIG. 5 is a view taken generally along line 5—5 of FIG. 4.
Figure 6:
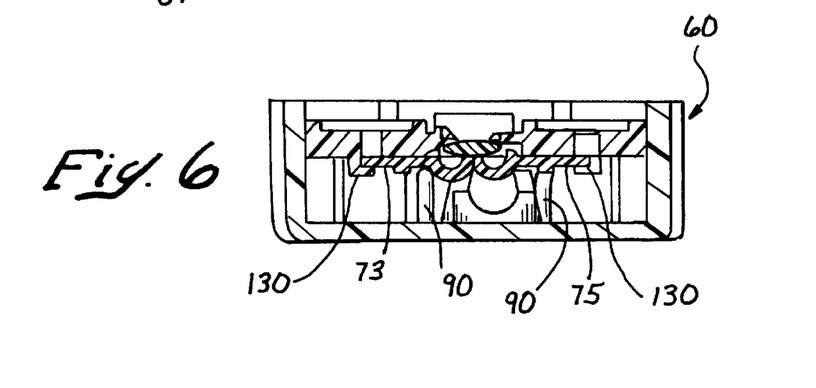
FIG. 6 is a cross sectional view of the combination shown in FIG. 3 with the intraocular lens holding assembly fully engaged with the intraocular lens injector holding assembly.

With particular reference to FIGS. 4 to 6, the combination of the holding member 14 and injector holder 60 is used as follows. With the holding member 14 withdrawn from the package system 10, and the injector 70 placed in the injector holder 60, the holding member and injector holder are brought together. As shown in FIG. 4, the holding member 14, in a planar position, that is with the hinge 116 in a neutral position, is placed so that the projections 102 on holder 60 are introduced into the through holes 140 of holding member 14. At this point, the end portion 144 of holding member 14 is in contact with each of the mounting members 108. In this configuration, the recess 40 is mated with the projection 112 (FIG. 3), thus assuring that the holding member 14 and injector holder 60 are properly oriented, and IOL 52 is substantially directly above the load chamber 72 of the injector 70, which is in an open position.

The holding member 14 is then rotated downwardly, that is pivoted around back end portion 144, so that the holding member comes in contact with the wings 73 and 75 of the injector being held in the injector holder 60. As this rotation occurs, the wings 73 and 75, supported by support members 90 are captured by the retaining members 130. In effect, the movement of the loading member 14 relative to the injector holder 60 proceeds so that, as shown in FIG. 6, the injector 70 is held or captured by the loading member 14. Thus, when the loading member 14 is removed from the injector holder 60, the injector 70 is removably secured to the holding member 14, as shown in FIG. 7.

With particular reference to FIG. 7, the lens holder 14, with the injector 70 removably secured thereto, is folded along hinge 116 and fold line 126 to cause the inserter 70 to move from the flat position shown in FIG. 6 to a more closed position shown in FIG. 7. The holding member 14 is folded until the hinge 116 can fold no more. At this point, the grasping fingers 138 of injector 70 are positioned around the edges of optic 50, which is still located in the internal groove 48.

Figures 8, 9:
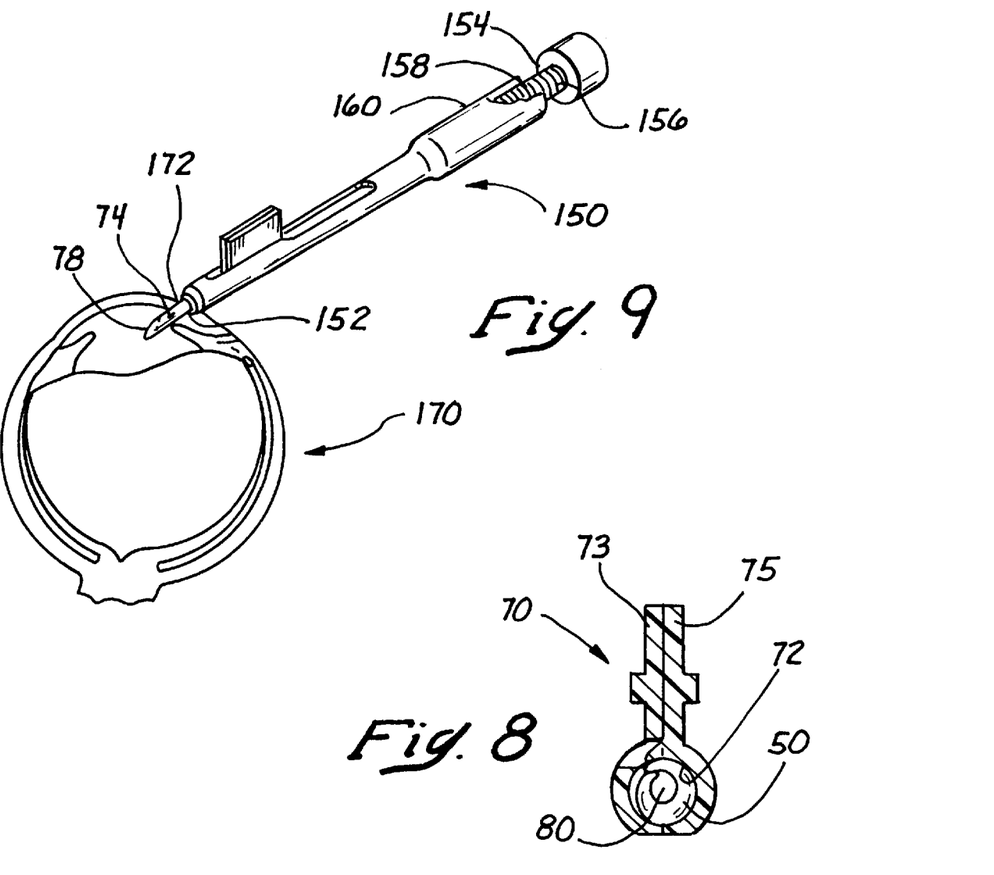
FIG. 8 is a cross sectional view of the intraocular lens injector with the folded IOL included.
FIG. 9 is a somewhat schematic illustration showing the IOL injector located in a handpiece being used to inject the IOL into an eye.

In this configuration, as shown in FIG. 7, the user grasps the wings 73 and 75 of injector 70 and removes the injector from the holding member 14. In so doing, the action of the grasping fingers together with the removing of the injector 70 from the holding member 14 also removes the IOL 52 from the holding member and places the IOL in the loading chamber 72. After the injector 70 is removed from the holding member 14, the two wings 73 and 75 are placed together, as shown in FIG. 8, to place the loading chamber 72 in a closed position with the folded optic 50 located therein. The filament haptics 53 and 55 are located generally parallel to, rather than transverse to, the longitudinal axis of injector 70. The inserter 70 is now ready to be used to insert the IOL 52 into an eye.

Although it is possible to reuse the holding member 14 and injector holder 60, preferably these components are disposed of after a single use.

An effective amount of a liquid composition, such as an aqueous balanced salt solution (BSS) and/or a visco elastic material, for example, an aqueous solution of sodium hyaluronate, other conventional visco elastic components, and the like and mixtures thereof, is added to the hollow space 80 facilitate the passage of the IOL 52 through the hollow space and into the eye. If desired, the liquid composition can be added to the load chamber 72 of injector 70 while the injector is held in injector holder 60.

With the injector 70 configured as shown in FIG. 8 the injector 70 is placed in association with hand piece 150. In this configuration, shown generally in FIG. 9, the distal end portion of injection tube 74 extends distally beyond the distal end 152 of hand piece 150.

With injector 10 so placed relative to hand piece 150, push rod member 154 is placed into the hollow space 80 starting at the proximal end. Prior to this step, the distal end of push rod member 154 is placed in tip holder 94 of injector holder 60 so that soft tip 96 is placed on the distal end of the push rod member. As threads 156 of push rod member 154 come in contact with and engage inner threads 158 of hand piece 150, the push rod member 154 is rotated, so as to thread the push rod member onto the proximal end portion 160 of hand piece 150. By gradually moving push rod member 154 through hollow space 80, the folded IOL 52 is urged to move through the hollow space, through open distal end 78 and into the eye.

The IOL 52 is to be placed in eye 170 into an area formerly occupied by the natural lens of the eye. The sclera 172 is shown having an incision through which the distal end portion of injection tube 74 is passed. Alternately, the incision can be made through the cornea. The distal end portion of the injection tube 74 preferably has a sufficiently small cross-section to pass into the eye 170 through a 3.0 mm incision in the sclera 172.

The injection tube 74 is manipulated within eye 170 until it is positioned so that IOL 52 can be properly positioned in eye 170, that is in the anterior chamber, the posterior chamber, the capsular bag or in the sulcus, after being released. Thus, the surgeon is able to controllably position the distal end portion of injection tube 74, with IOL 52 in the hollow space 80. Once distal end portion of injection tube 74 is so positioned, the rod member 154 is urged distally to pass the IOL 52 through the hollow space 80, through the open distal end 78 of injection tube 74 and into the eye 170.

After the IOL 52 has been inserted into the eye, the push rod member 154 is moved proximally into the injection tube 74 and the distal end portion of the injection tube is removed from the eye. If needed, the IOL 52 can be repositioned in the eye by a small, bent needle or similar tool inserted into the same incision.

Once the IOL 52 is properly positioned in eye 170 and injector 70 is withdrawn from the eye, the incision in the sclera may be mended, for example, using conventional techniques. After use, injector 70 preferably is disposed of. Hand piece 150 and push rod member 154 can be reused, after sterilization/disinfection.

While this invention has been described with respect of various specific examples and embodiments, it is to be understood that the invention is not limited thereto and that it can be variously practiced within the scope of the following claims.

What is claimed is:

1. An apparatus for holding an intraocular lens injector, the apparatus comprising:

a housing holding an intraocular lens injector having a proximal end and an opposing hollow injection tube, through which an intraocular lens is passed into an eye, having a single configuration and being secured to the proximal end; and a plurality of elements secured to the housing, and structured and adapted to hold the intraocular lens injector to the housing, provided that at least one of the elements is positioned to contact the injection tube.

2. The apparatus of claim 1 wherein the intraocular lens injector has a proximal end and one or more of the elements are positioned to be in proximity to the proximal end.

3. The apparatus of claim 1 wherein the intraocular lens injector includes a pair of movable, generally opposing wings, and the apparatus further comprises at least one support member secured to the housing and positioned so that at least one support member is in proximity to each of the wings of the intraocular lens injector held by the housing.

4. The apparatus of claim 1 wherein the housing includes a base and the at least one element is secured to the base.

5. The apparatus of claim 4 wherein the housing includes a sidewall extending from the base.

6. The apparatus of claim 5 wherein the sidewall is a peripheral sidewall.

7. The apparatus of claim 5 wherein the sidewall includes at least one projection extending inwardly and the apparatus further comprises at least one mounting member secured to the housing and spaced apart from the at least one projection.

8. The apparatus of claim 7 which includes two of the projections and two of the mounting members positioned so that each projection is aligned with and spaced apart from a different one of the mounting members.

9. The apparatus of claim 1 which further comprises a tip holder secured to the housing, the tip holder being adapted to hold a tip to be placed on a distal end of a push rod used in inserting an intraocular lens into an eye.

10. The apparatus of claim 1 which comprises a polymeric material.

11. A method of loading an intraocular lens into an injector in preparation for inserting the intraocular lens into an eye, the method comprising:

providing a deformable intraocular lens in an intraocular lens holding assembly adapted for removably retaining the intraocular lens;

providing an injector held in an intraocular lens injector holding assembly including a housing adapted to hold the injector;

positioning the intraocular lens holding assembly in close proximity to the housing;

effecting a direct transfer of the injector from the intraocular lens injector holding assembly to the intraocular lens holding assembly; and removing the injector and the intraocular lens together from the intraocular lens holding assembly.

12. The method of claim 11 wherein the injector has a loading chamber and the injector step is effective to provide the injector held in the intraocular lens injector holding assembly with the loading chamber maintained in an open position.

13. The method of claim 12 wherein during or after the removing step, the loading chamber is placed in a closed position.

14. The method of claim 11 wherein the effecting step comprises moving the intraocular lens holding assembly relative to the housing to effect the direct transfer.

* * * * *

UNITED STATES PATENT AND TRADEMARK OFFICE
CERTIFICATE OF CORRECTION

PATENT NO.     : 6,447,519 B1
DATED          : September 10, 2002
INVENTOR(S)    : Brady et al.

It is certified that error appears in the above-identified patent and that said Letters Patent is hereby corrected as shown below:

Column 6,
Line 46, "structures" should read -- structure --.

Column 12,
Line 42, "and the injector step" should read -- and providing the injector step --.

Signed and Sealed this

Third Day of June, 2003

JAMES E. ROGAN
*Director of the United States Patent and Trademark Office*